United States Patent [19]

Westphal

[11] Patent Number: 4,856,497

[45] Date of Patent: Aug. 15, 1989

[54] PORTABLE COLLAPSIBLE TREATMENT TABLE WITH DROP SECTIONS

[75] Inventor: Donald J. Westphal, South Elgin, Ill.

[73] Assignee: Standex International Corporation, Salem, N.H.

[21] Appl. No.: 119,791

[22] Filed: Nov. 12, 1987

[51] Int. Cl.⁴ ........................ A61F 5/00

[52] U.S. Cl. ........................ 128/70; 128/69

[58] Field of Search ........................ 128/69-74; 108/34; 297/377, 353

[56] References Cited

U.S. PATENT DOCUMENTS

| | | | |
|---|---|---|---|
| 1,180,822 | 4/1916 | Broberg | 120/71 |
| 1,184,660 | 5/1916 | Rhine | 128/72 |
| 1,210,878 | 1/1917 | Weber | 297/377 |
| 1,230,592 | 6/1917 | Montaney | 128/73 |
| 1,499,013 | 6/1924 | Gunther | 128/72 |
| 1,530,719 | 3/1925 | Harris | 128/74 |
| 1,626,091 | 4/1927 | Macklin | 128/74 |
| 1,908,778 | 5/1933 | Memminger | 128/73 |
| 2,023,248 | 12/1935 | Skillman | 128/70 |
| 2,054,732 | 9/1936 | Saffry | 128/72 |
| 2,216,317 | 10/1940 | Kansh | 297/377 |
| 2,517,681 | 8/1950 | Koerper | 128/70 |
| 2,579,783 | 12/1951 | Branto | 128/70 |
| 2,702,909 | 3/1955 | Atkins | 297/377 |
| 2,819,132 | 1/1958 | Rock | 128/70 |
| 3,092,102 | 6/1963 | Thompson | 128/70 |
| 3,315,667 | 4/1967 | Yoder | 128/71 |
| 3,423,773 | 1/1969 | Yamate | 128/70 |
| 4,230,100 | 10/1980 | Moon | 128/70 |
| 4,334,710 | 6/1982 | Milnar, Jr. | 297/377 |
| 4,404,966 | 9/1983 | Hartman | 128/69 |
| 4,660,237 | 4/1987 | Brodnax | 297/377 |
| 4,684,170 | 8/1987 | Colby | 297/377 |
| 4,732,141 | 3/1988 | Steffensmeier | 128/70 |
| 4,749,230 | 6/1988 | Tornero | 297/353 |

FOREIGN PATENT DOCUMENTS

| | | | |
|---|---|---|---|
| 1145947 | 10/1957 | France | 297/377 |

*Primary Examiner*—Edgar S. Burr
*Assistant Examiner*—Tonya Lamb
*Attorney, Agent, or Firm*—Mason, Kolehmainen, Rathburn & Wyss

[57] ABSTRACT

A portable treatment table comprises a plurality of separate patient support table sections interconnectable for supporting a patient during treatment at a convenient working level above the floor while lying in a generally horizontal position. Each of the table sections includes a cushion assembly with drops for supporting a portion of the patient's body mounted on a frame and a plurality of support legs are pivotally interconnected with the frame for movement between a folded-up position inside the frame for transporting the table sections and a downwardly extended position for supporting the patient during treatment. Connectors are provided for detachably interconnecting the frames of the table sections and a detachable head piece assembly is provided for supporting a patient's head for cervical adjustment while lying on the interconnected table sections. When not in use, the head piece assembly is stowed for transport beneath the cushions of the table sections inside the folded-up legs and frame.

26 Claims, 9 Drawing Sheets

30

Fig. 18
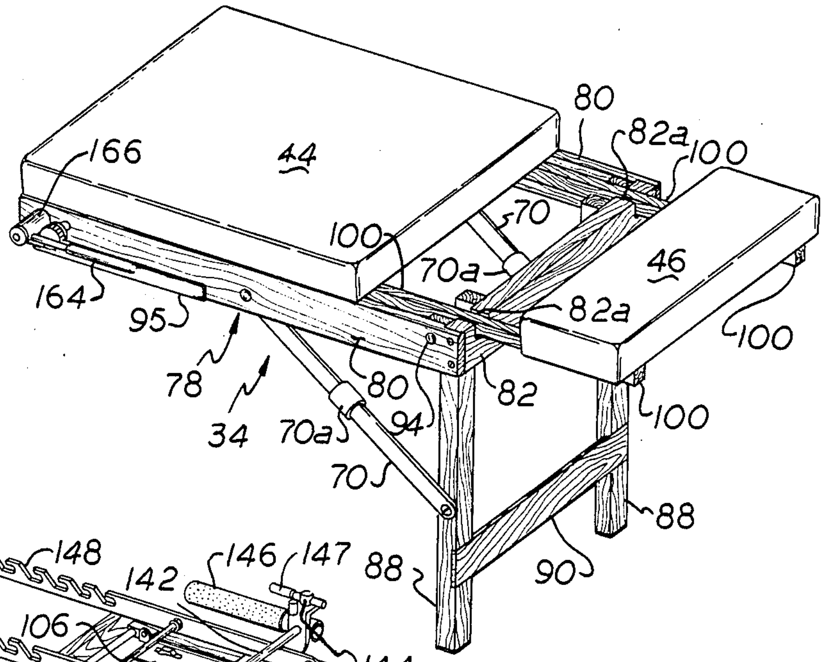
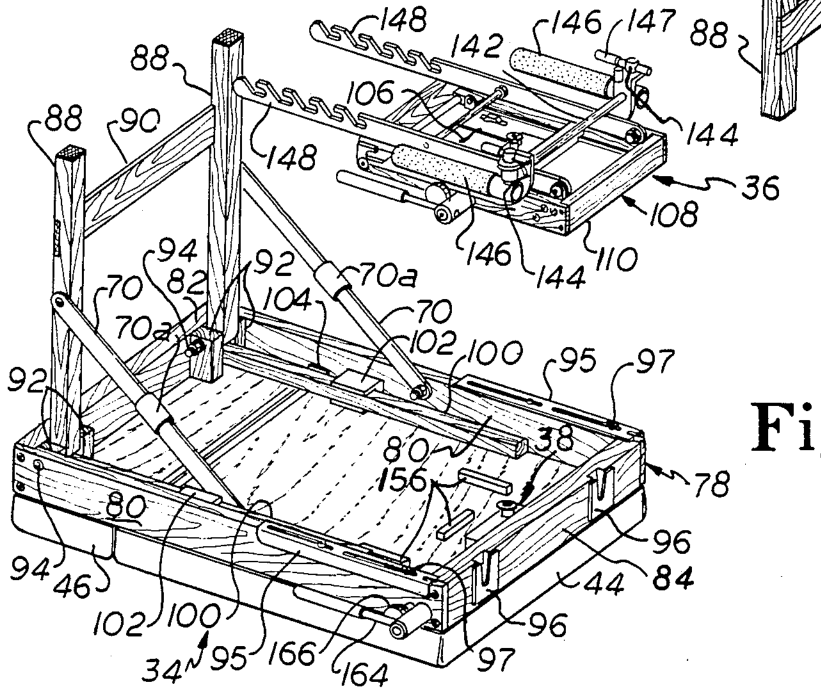
Fig. 19
Fig. 20
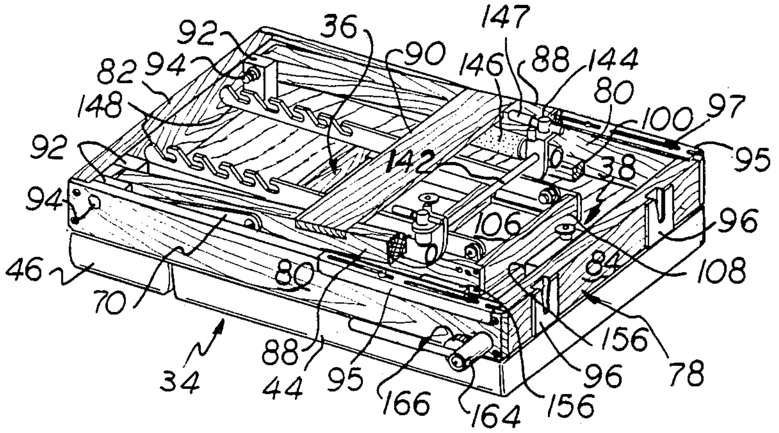

PORTABLE COLLAPSIBLE TREATMENT TABLE WITH DROP SECTIONS

BACKGROUND OF THE INVENTION

1. Field of the Invention

The present invention relates to a new and improved portable treatment table and more particularly to a portable treatment table especially designed for use by chiropractors for the treatment of patients at locations remote from the doctor's office or treatment center. The portable chiropractic treatment table is designed to make it practical for a chiropractor or doctor to transport the table from place to place in a folded-up condition yet still provide a full range of cervical, thoracic and pelvic adjustments including drops. The table is also useful in sports medicine applications and in nursing and convalescent homes where patients are unable to travel to a chiropractor's regular clinic or office. 2. Background of the Prior Art Over the years, a wide variety of chiropractic treatment tables have been developed and some of them have included complex and heavy mechanisms designed to provide a wide range of chiropractic adjustments on a patient during treatment. These tables are usually made of metal, are relatively large and heavy and do not lend themselves readily to movement or transportation from place to place once the tables are fully assembled ready for use. Thus, with tables heretofore existing, it has been impractical for a chiropractor to use a full feature table to make house calls or to service immobile patients residing in nursing homes and the like, or to attend athletic and sports events for the treatment of sports injuries on the spot.

OBJECTS OF THE INVENTION

Accordingly, it is an object of the present invention to provide a new and improved portable treatment table and more particularly a portable chiropractic patient treatment table which is small enough in size and light enough in weight to be transportable from place to place as needed.

Another object of the invention is to provide a new and improved portable treatment table of the character described which can be easily and rapidly assembled from a folded-up transport position into a patient treatment position ready for the care and treatment of chiropractic patients at remote locations.

Yet another object of the present invention is to provide a new and improved chiropractic treatment table of the character described which is portable and thus well-suited for use in house calls, sports medicine and nursing and retirement facilities away from the using practitioner's office or clinic.

Still another object of the present invention is to provide a new and improved portable treatment table which is useful for cervical adjustments to a patient in a sitting position thereon.

Still another object of the present invention is to provide a new and improved portable chiropractic treatment table of the character described which includes a detachable head piece assembly having a drop capability for cervical adjustments, a front table section, employing dorsal and lumbar cushions with drops provided and a pelvic section attachable thereto with a drop so that pelvic drop adjustments may be made as desired.

Another object of the present invention is to provide a new and improved portable chiropractic treatment table of the character described having a head piece assembly which is attachable to a floor supported portable table section and which is adjustable to provide a plurality of different levels relative to the table section and a plurality of different angular slopes relative thereto.

Yet another object of the present invention is to provide a new and improved table section useful for treatment of patients in a sitting position.

More particularly, it is an object of the present invention to provide a new and improved chair of the character described which additionally serves as a front table section in a multi-section portable chiropractic treatment table system.

Yet another object of the present invention is to provide a new and improved portable chiropractic treatment table of the character described which is relatively low in cost, simple and easy to assembly and disassemble and relatively light in weight and small in size so as to be suitable for transporting for house calls, and for sports medicine and nursing home application.

BRIEF SUMMARY OF THE INVENTION

The foregoing and other objects and advantages of the invention are accomplished in an illustrated embodiment comprising a new and improved portable treatment table including a plurality of separate patient supporting table sections which are interconnectable for supporting a patient for treatment at a convenient working level above the floor while the patient is supported in a generally horizontal lying position. Each of the table sections includes a cushion assembly for supportig a portion of the patient's body and the assembly is mounted on a frame supported by a plurality of legs pivotally interconnected to the frame for movement between a folded-up position inside the frame for transportation of the table sections and a downwardly extended position for engaging the floor to support the cushion at a suitable level for patient treatment. Connectors are provided for detachably interconnecting the frames of the table sections and a detachable head piece assembly is provided for attachment to one of the table sections to support the head of a patient lying on the cushions of the interconnected table sections. Lift and drop assemblies are provided for the head piece, a dorsal cushion, a lumbar cushion and a pelvic cushion of the table sections and an ankle support cushion is slideably adjustable for patients of differing heights.

BRIEF DESCRIPTION OF THE DRAWINGS

For better understanding of the present invention, reference should be had to the following detailed description taken in conjunction with the drawings, in which:

FIG. 18 is a perspective view of a pelvic table section of the table constructed in accordance with the features of the present invention and illustrating an ankle support cushion thereon in an extended position;

FIG. 19 is a view of the underside of the pelvic table section and a head piece assembly detached and ready for stowage on the underside of the pelvic cushion;

FIG. 20 is an underside view of the pelvic table section with the head piece assembly stowed and the legs in a folded position ready for transport;

DETAILED DESCRIPTION OF THE PREFERRED EMBODIMENTS

Figure 1:
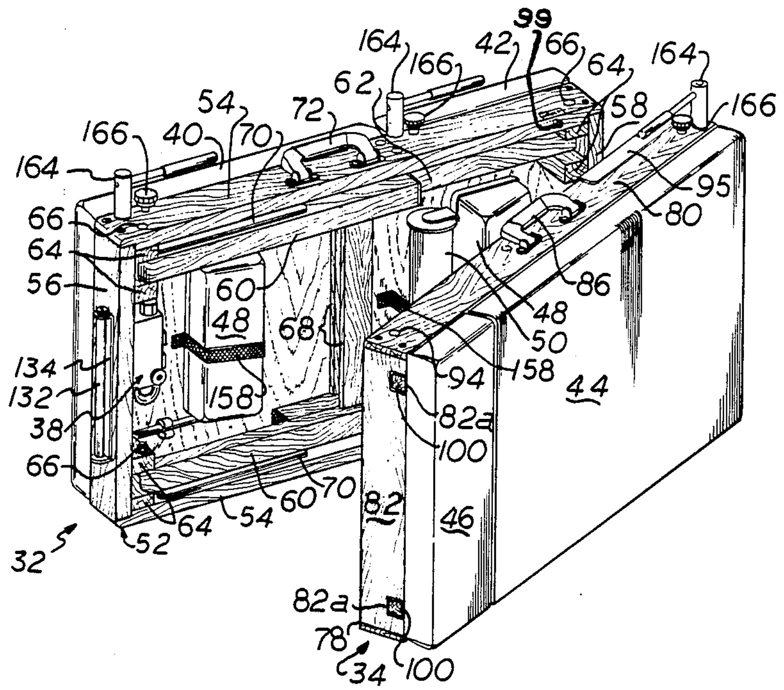
FIG. 1 is a perspective elevational view of a new and improved portable treatment table shown in a folded-up condition ready for transport.
Figure 2:
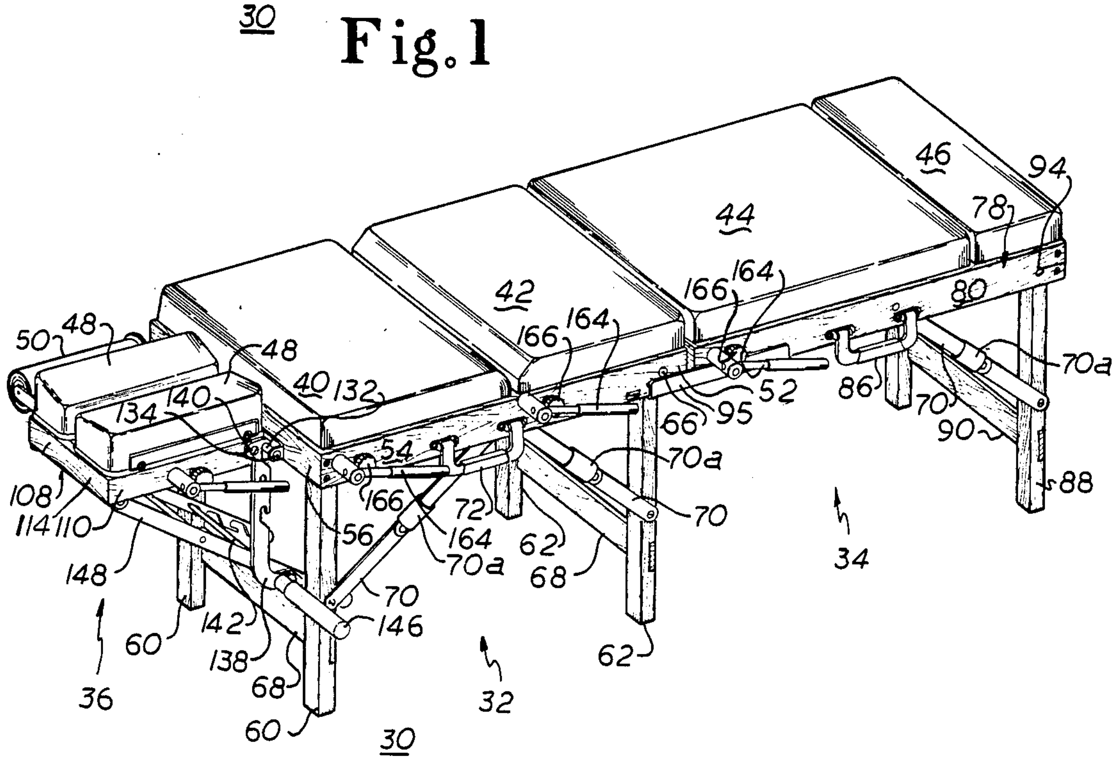
FIG. 2 is a perspective view of the table of FIG. 1 shown in an assembled condition ready for receiving a patient for treatment.

Referring now more particularly to the drawings and initially to FIGS. 1 and 2, therein is illustrated a new a improved portable treatment table especially designed and adapted for use by a chiropractor for treating patients at home and at other locations remote from the office such as sporting events, nursing homes, etc. The portable treatment table as a whole is generally referred to by the reference numeral 30 and includes a generally rectangular shaped front or thoracic table section 32, a pelvic table section 34 and a detachable head piece assembly 36 designed to support a patient's head while the patient is lying prone in a horizontal position on the assembled table as illustrated in FIG. 2.

As illustrated in FIG. 1, each of the table sections 32 and 34 is dimensioned to occupy a space about the size of an ordinary suitcase so that both table sections may be handled and transported by one person and with the removable head piece assembly 36 in a stowed position on the respective table sections. The table is constructed to be relatively low in weight so that the suitcase sized table sections may be carried from place to place without undue burden to remote locations for patient treatment and then the components assembled together to provide a treatment table as shown in FIG. 2 capable of use for a wide range of functions by the chiropractor in treating a patient.

Figure 21:
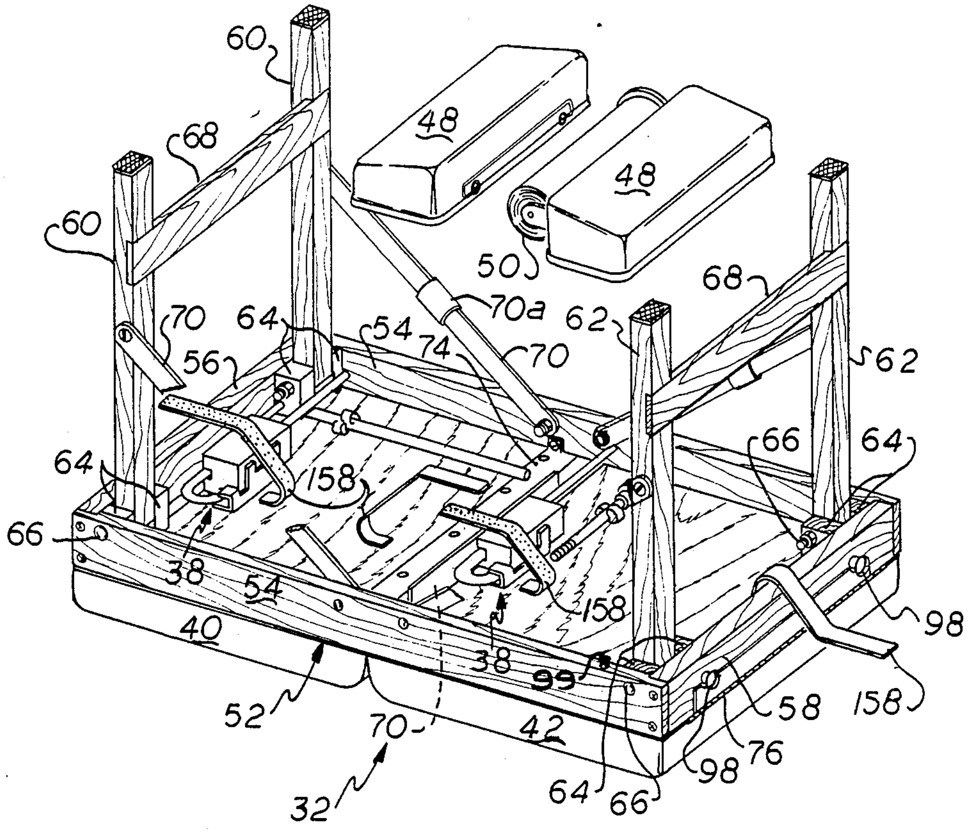
FIG. 21 is a perspective view of the underside of the front table section of the table with the legs in an extended position and the head piece cushions detached from the head piece frame and ready for stowage.

Each table section 32 and 34 and the head piece assembly 36 has one or more independently controllable lift and drop assemblies 38 to provide drop adjustments for patients requiring a pelvic drop, a cervical drop, a dorsal drop or a lumbar drop. In order to support a patient for treatment in a horizontal, generally prone position, the front table section 32 is provided with a dorsal cushion 40 of generally rectangular shape and a lumbar cushion 42. The pelvic table section 34 is provided with a relatively large pelvic cushion 44 and a smaller sized ankle support cushion 46 adjacent the foot end of the assembled table. In addition, the head piece assembly 36 is provided with a pair of spaced apart, longitudinally extending face support cushions 48 which are detachable from the framework of the head piece assembly and which are stowable separate and independently on the bottom side of the front table section 32 below the dorsal cushion 40 and lumbar cushion 42. This is shown in FIG. 1 which depicts the table after being disassembled and folded-up ready for transport. As illustrated in FIGS. 1, 2 and 21, one of the removable face support cushions 48 is provided with a paper roll support assembly 50 adjacent an outside edge surface for dispensing paper placed across the upper surfaces of the face support cushions so that each new patient has a clean and sterile paper surface to rest upon during treatment.

Front Table Section

The front or thoracic table section 32 includes a rectangular frame 52 comprising parallel opposite side rails 54 joined together at a head end by a cross member 56 and at the opposite end by a parallel cross member 58. Preferably, the rails and cross members are formed of lightweight, strong, hardwood and the frame serves as a protective enclosure or casing along with the cushions 40 and 42 for components which are stored within the frame as illustrated in FIGS. 1 and 22 when the table section is folded-up ready for transport or storage.

Figure 3:
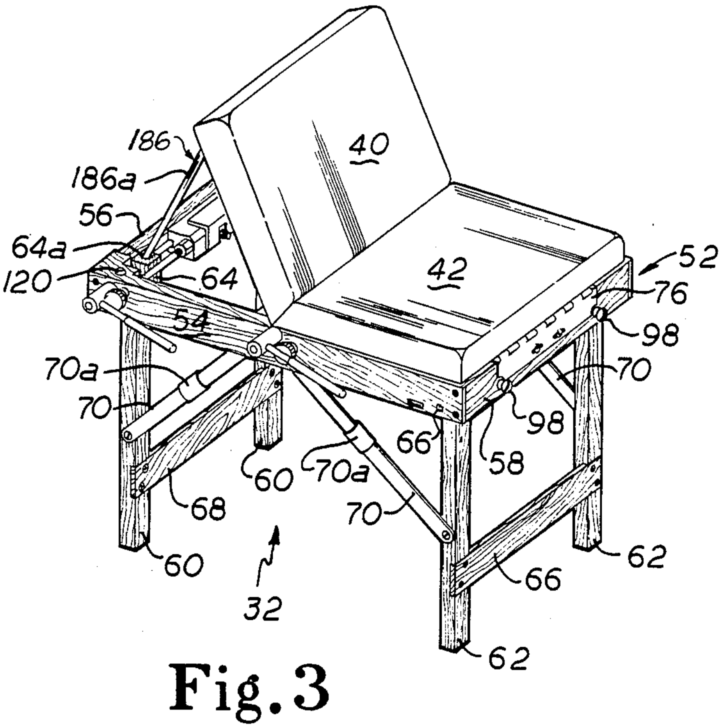
FIG. 3 is a perspective view of one of the portable table sections shown in an erected condition suitable for use in making cervical adjustments on a patient.

In accordance with the present invention, the front table section is provided with two pairs of folding legs 60 and 62. The upper end portion of the respective pairs of legs 60 and 62 are sandwiched between pairs of short corner blocks 64 and are mounted for pivotal movement on pivot bolts 66 extending between and through the corner blocks and an adjacent side frame member 54. Each pair of legs is pivotal between a folded-up position within the rectangular frame 52 as shown in FIG. 1 for the transport or storage of the table and an extended, downwardly depending position as shown in FIGS. 2, 3–8, 15–18 and 21 for supporting the table cushions 40 and 42 at a convenient working level above the floor for the treatment of a patient. Each pair of legs is braced with a cross member 68 adjacent the lower end portion to provide additional stability in a lateral direction for the table structure when the legs are extended downward for supporting the table. The cross members provide for increased lateral table stability and longitudinal stability for the table section 32 while the legs are in a downwardly extended position is provided by a mid-jointed, metal angle brace 70 for each leg, pivotally interconnected to the leg intermediate the length thereof at a lower end and pivotally connected to a side frame member 54 at the upper end. The mid-jointed metal braces are pivotally interconnected at the center at a pivotal junction between a lower brace member and an upper brace member and a locking sleeve 70a is longitudinally slideable into place over the intermediate joint of the angle brace to lock the lower and upper segments into longitudinal alignment when the legs are extended as shown in FIGS. 2 and 3. Metal braces 70 are formed to provide an overcenter limit to brace the extended legs of the table sections.

Figure 22:
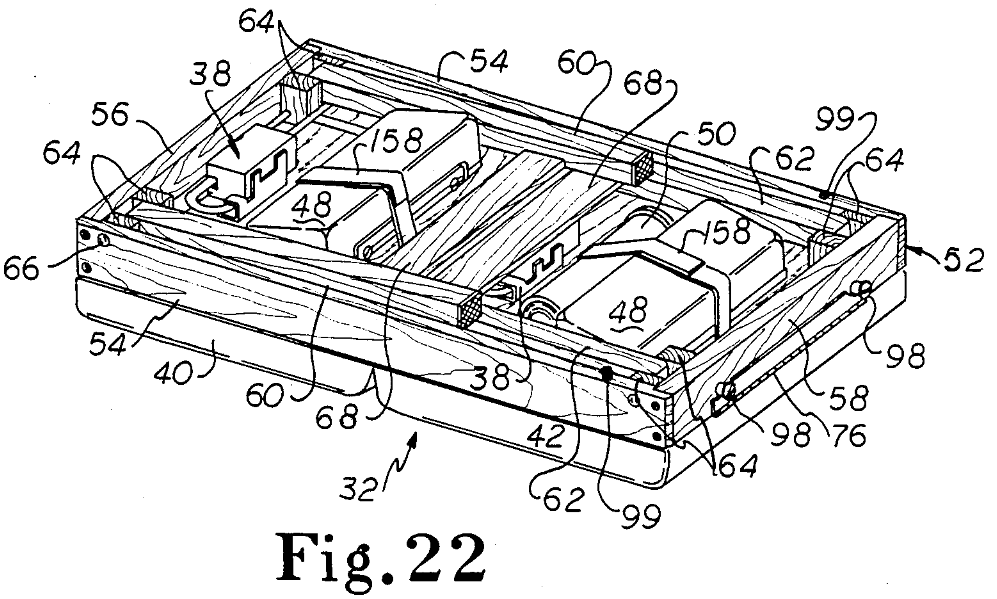
FIG. 22 is a perspective view of the underside of the front table section with the head piece cushions in the stowed condition and the support legs folded-up within the frame ready for transport.

When the legs are in the folded-up position as shown in FIGS. 1 and 22, the jointed angle braces fold up at the middle and occupy a space between the outside edge of a leg and the adjacent inside face of the side rail 54. In order to fold up the legs after they have been extended and locked in place with the sleeves 70a, it is only necessary to move the sleeves 70a upwardly onto the metal brace section and then pivot the upper and lower metal braces about the middle joint while the legs themselves are pivoted from the extended position (FIG. 2) towards the folded-up position as shown in FIG. 1. When folded-up, the legs 60 and 62 nest neatly within the interior of the rectangular frame 52 supporting the cushions 40 and 42 and the front table section thus appears similar to a suitcase in size and can be readily transported by a handle 72 which is secured to one of the side frame members as shown in FIGS. 1 and 2.

Referring now more particularly to FIGS. 3, 15–17, 21 and 22, the dorsal and lumbar cushions 40 and 42 are secured to the frame 52 for pivotal movement along respective transverse edges of the cushions by elongated piano-wire type hinges 74 and 76, respectively, so that the each cushion can be lifted upwardly to an elevated position (FIG. 15) to provide a dorsal drop and a lumbar drop when desired for patient treatment. A lift and drop assembly 38 is provided for each of these cushions and also is provided for the head piece assembly 36 and the pelvic cushion 44 as shown in FIGS. 9, 10, 12–17, 21 and 22. Each of the lift and drop mechanisms 38 is substantially identical to the others and, in general, the drop mechanisms are of a type disclosed in U.S. Pat. No. 3,092,102 to Thompson.

Pelvic Table Section

The pelvic table section 34 is generally similar to the thoracic table section 32 but does have some significant differences which will be discussed in greater detail hereinafter. The pelvic table section includes a rectangular frame 78 formed with a pair of opposite side rails 80 interconnected by a transverse cross member 82 at the foot or outer end and a cross member rail 84 at the opposite, inner end. Like the front table section, the pelvic table section 34 includes a handle 86 attached to one of the side rails 80 for carrying the unit in a folded-up condition. The pelvic table includes only a single pair of legs 88 at the foot end which are stiffened in a lateral direction by a cross member 90 similar to the cross member 68. Each leg 88 is pivotally attached to the frame 78 adjacent the foot end cross member 82 between a pair of short corner blocks 92 and pivot bolts 94 extend through the corner blocks and the upper end portions of the legs to support the same for pivotal movement between a folded-up position (FIG. 20) stowed between the rails of the frame 78 ready for transport when the table section is ready for transport. Each leg 88 is also secured in a downwardly depending position as shown in FIGS. 2 and 19 by means of a jointed metal angle brace 70 having a locking sleeve 70a for locking the middle joint when the legs are extended. Metal braces 70 are formed to provide an overcenter limit. An upper member of each jointed metal brace is pivotally secured to a side rail 80 of the frame and a lower member of the angle brace is pivotally connected to the leg 88 intermediate its ends.

Only one pair of legs 88 is required for the pelvic table section because this section is operationally attached to the front table section 32 when the table 30 is fully assembled together as shown in FIG. 2, the inner end portion of the table section 34 is then supported by the legs 62 on the thoracic table section 32. For the purpose of interconnecting together the table sections 32 and 34 in readiness for a patient, the inner cross member 84 of the pelvic table section is provided with a pair of slot members 96 formed of metal and spaced apart on the outer surface of the cross member with downwardly extending slots therein aligned with slotted out portions provided in the wooden cross member 84. The slotted plate connectors are adapted to slideably engage and detachably connect the table sections together by fitting over a pair of similarly spaced apart, headed fasteners 98 (FIG. 3) projecting outwardly from the inner end, cross member 58 of the thoracic table section 32.

Once the legs are extended on both of the table sections as illustrated, attachment of the pelvic table section 34 to the table section 32 is made fast and simple by entering the slots of the connector plates 96 above the extended, headed fasteners 98 and moving the cushion 44 of the pelvic table section downwardly. The slots provided in the connectors 96 are slightly tapered and a retainer leaf spring is located behind the tapered plates to engage the fasteners 98 to provide a wedging effect for holding the tables tightly together in a unitary assembly as shown in FIG. 2, thereby providing a serial array of cushions 40, 42, 44 and 46 for supporting the body of a patient for treatment in a horizontal, prone position. To further insure locked engagement of table sections, a slotted angle 95 is slideably mounted on the lower edge of each side rail 80 and is held in place with a wing nut 97. These angles are slid forward to engage screws 99 on the front section side frame members 54 as shown in FIGS. 1, 2, 18 and 19 to align and hold the table frames together. To disconnect the table sections 32 and 34, the cross member 78 of the pelvic table section is simply raised while holding the frame of the adjacent thoracic table section down until the connector plates 96 are moved upwardly out of engagement with the protruding headed fasteners 98.

In accordance with the present invention, the ankle support cushion 46 of the pelvic table section 34 is designed to slide longitudinally of the side rails 80 of the table frame 78 and for this purpose, the cushion is mounted on a pair of elongated slides 100 (FIG. 18) which are supported and guided for sliding movement in notches or openings 82*a* formed in the end member 82 on the upper edge below the underside of the ankle support cushion. Inner end portions of the slides 100 are supported and guided in channel-shaped guide blocks 102 fastened to the inside surface of the opposite side rails 80. Whenever patients of greater than average height are treated, the ankle cushion 46 may be pulled outwardly and the slides provide support for the cushion in spaced apart relation to the cushion 44 (FIG. 18) in a cantilever fashion.

When the pair of legs 88 of the pelvic table section 34 are pivoted to the folded-up position as shown in FIG. 20, interiorly thereof adjacent the underside of the cushions 44 and 46, there is provided a space for stowage of a portion of the head piece assembly 36 so that the disconnected head piece assembly and pelvic table section can be conveniently readily transported from place to place as needed. The large pelvic cushion 44 is pivotally secured to the wooden frame 78 of the pelvic table section by a pair of brackets 104 fastened to the base of the cushion and pivotally attached to mounting screws on the inside face of the side frame rails so that the end of the pelvic cushion 44 adjacent the front table section may be lifted to an elevated position like the cushions 40 and 42 by operation of a lift and drop assembly 38 which will be described hereinafter.

Head Piece Assembly

The head piece assembly 36 is adapted to be detachably mounted on the assembled table (FIG. 2) adjacent the head end cross member 56 of the thoracic table section 32 when the table is assembled and ready for treatment of a patient. When the table is not in use and is ready for transport and/or storage, the head piece assembly is disassembled from the table sections 32 and portions thereof are stowed within the frame and legs of the respective front table section 32 and pelvic table section 34 while the legs are in a folded-up condition. As previously noted, the head piece assembly includes a pair of facial support cushions 48 and a paper roll assembly 50 attached to one of the face cushions. These cushions are detachably mounted on a metal base plate 106 (FIGS. 6–11) which base plate, in turn, is supported for movement toward and away from a rectangular-shaped wooden frame 108 similar to the frames 52 and 78 of the table sections 32 and 34 but somewhat smaller in size. The wood frame 108 includes a pair of side rails 110 joined at opposite ends by transverse cross members 112 and 114 and as shown in FIG. 10, an intermediate cross member 116 is provided for supporting a lift and drop assembly 38 to provide for cervical drop adjustments. Each of the removable head cushions 48 is provided with a flat rigid base element 48*a* for detachably mounting the element on the base plate 106. Latch assemblies 118 are provided to latch and hold the cushions 48 in place on the base plate.

Referring to FIGS. 4–8, when the head cushion subassembly mounted on the plate 106 is in a lower position, the underside of the plate is supported from the frame 108 on a plurality of rubber shock mounts 120 spaced around the perimeter of the frame. These shock mounts also serve to cushion the drop when the lift and drop mechanism 38 is actuated to provide a cervical drop adjustment on a patient during treatment. Similar shock mounts 120 are provided between the wooden rectangular frames 54 and 80 of the front and the pelvic table sections 32 and 34, respectively, to cushion the end of a drop when effected by downward pressure on a respective dorsal cushion 40, a lumbar cushion 42, or a pelvic cushion 44, as the case may be.

Figure 8:
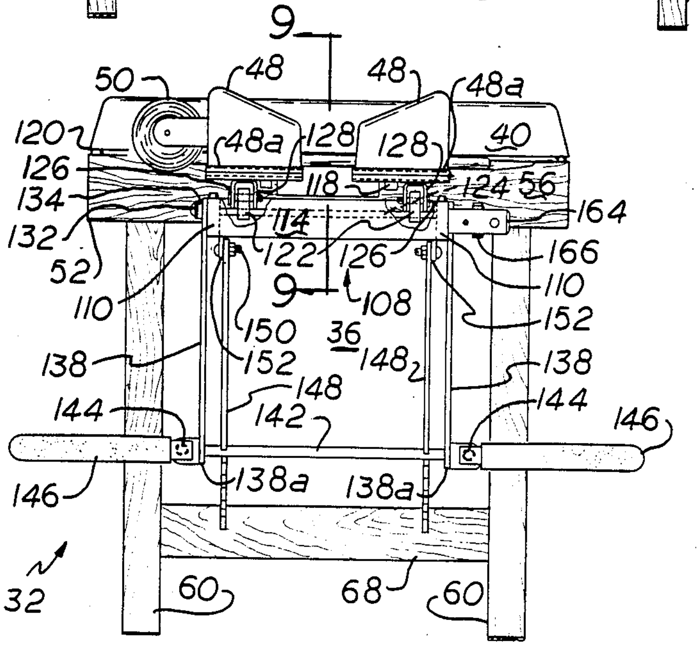
FIG. 8 is a head end elevational view of the table and head piece assembly thereof.
Figure 9:
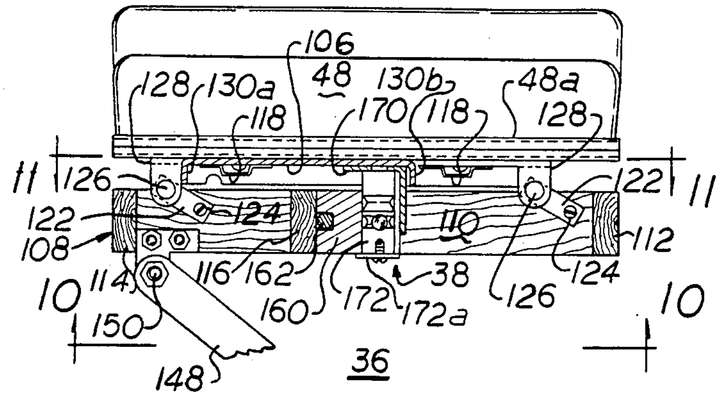
FIG. 9 is a fragmentary longitudinal cross-sectional view of the head piece assembly of the table illustrating a lift and drop mechanism and showing the head piece cushion in an elevated position ready for a rapid drop.
Figure 10:
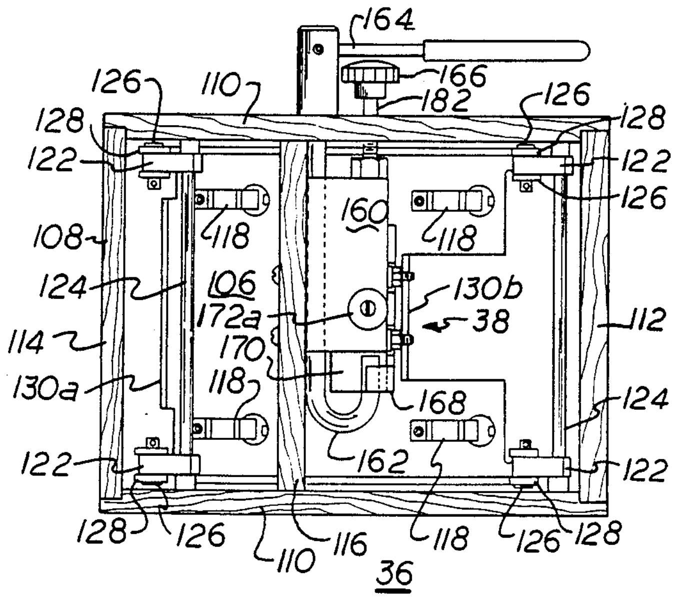
FIG. 10 is a bottom view of the head piece assembly looking upwardly in the direction of arrows 10—10 of FIG. 9.
Figure 11:
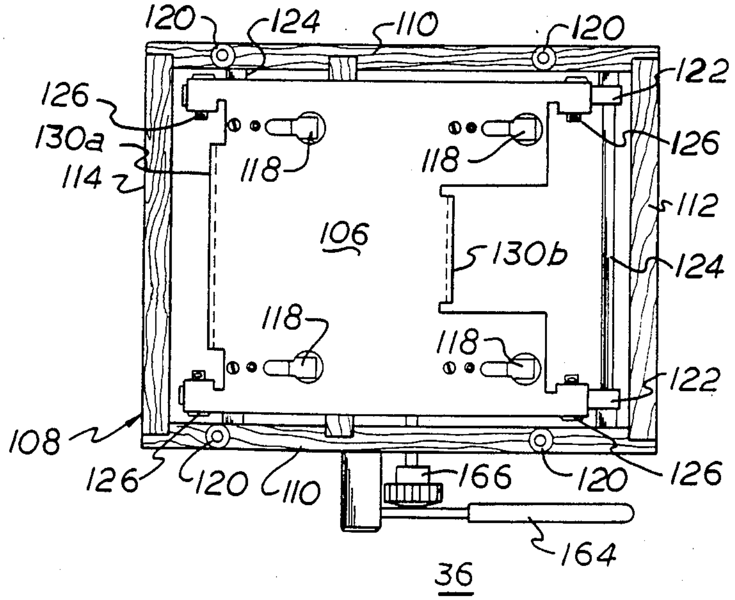
FIG. 11 is a cross-sectional view of the head piece taken substantially along lines 11—11 of FIG. 9.
Figure 12:
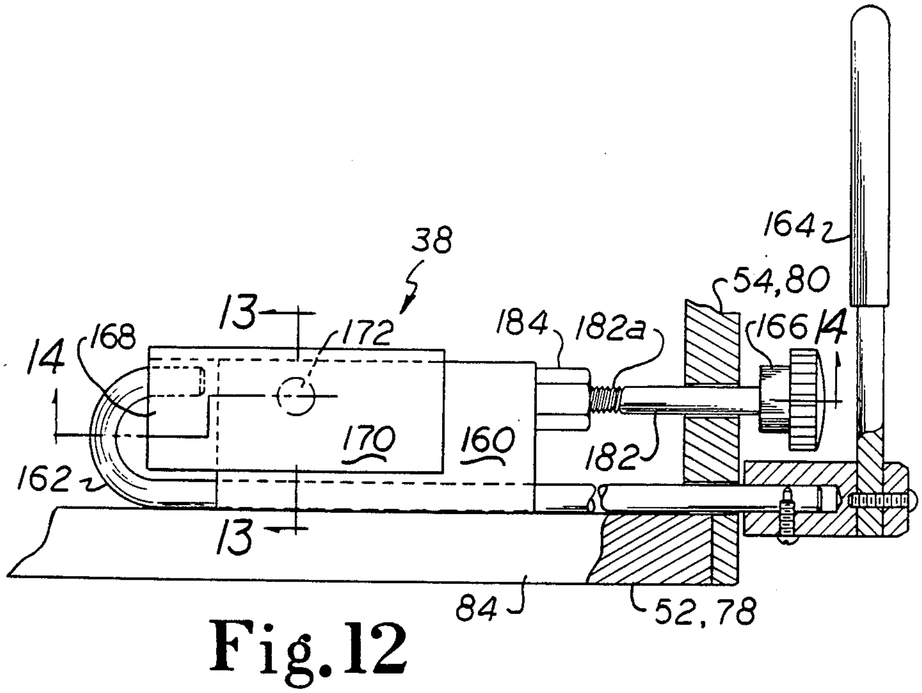
FIG. 12 is a fragmentary horizontal cross-sectional view of a lift and drop mechanism utilized in the table on the head piece assembly and the respective table sections.
Figure 13:
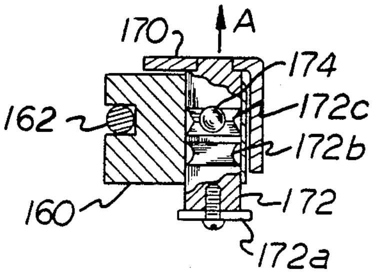
FIG. 13 is a fragmentary cross-sectional view taken substantially along lines 13—13 of FIG. 12.
Figure 14:
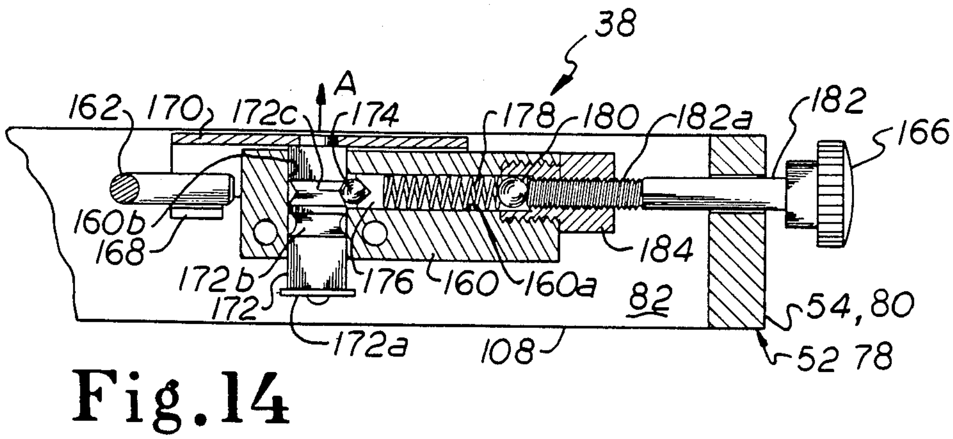
FIG. 14 is a transverse fragmentary cross-sectional view taken substantially along lines 14—14 of FIG. 12.
Figure 15:
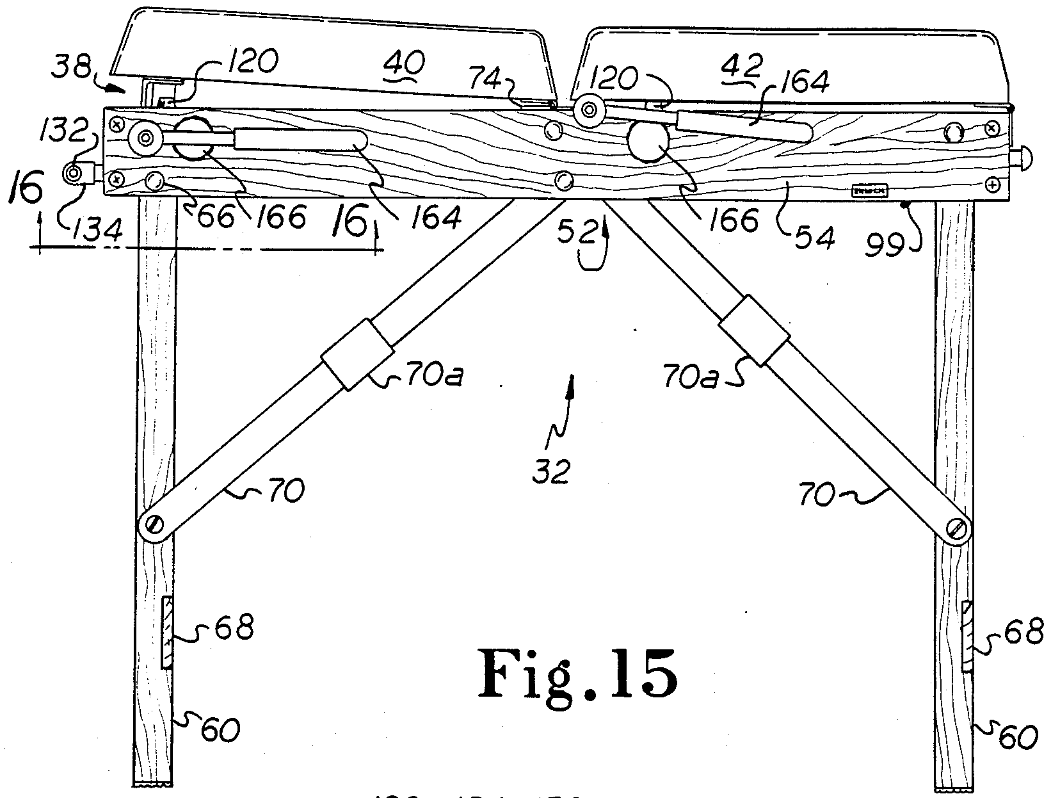
FIG. 15 is a side elevational view of a head end portion of a front table section of the table showing a dorsal cushion thereof in an elevated position ready for drop.

Referring now more particularly to FIGS. 8–11, the upper base plate 106 of the head piece assembly 36 is supported from the rectangular wooden frame 108 for upward elevation and downward dropping action by means of a plurality of short toggle links 122 pivotally interconnected at their lower ends to pairs of rod axles 124 extending parallel of the cross members 112, 114 and 116 between opposite side rails 110. At the upper end the toggle links 122 are pivotally connected through pins 126 to U-shaped brackets 128 (FIGS. 8 and 9) on the underside of the metal mounting plate 106 adjacent the four corners thereof. This arrangement permits the mounting plate 106 to be elevated upwardly to a position as shown in FIG. 9 and then subsequently dropped to a downward position as shown in FIGS. 4, 5, 6 and 7 to effect a cervical drop adjustment on a patent lying on the table with his head supported on the face cushions 48. The upper U-shaped brackets 128 are integrally formed on the base 106 which also carries latches 118 and has depending flanges 130*a* and 130*b* as shown in FIGS. 9 and 10.

Referring now specifically to FIGS. 4–8, the upper surface of the head cushions 48 can be aligned at a variety of different levels with respect to the upper surface of the body supporting cushions 40, 42, 44 and 46 on the rest of the table and in addition the head cushions may be aligned to slope upwardly or downwardly from a generally horizontal alignment as desired to effect the proper cervical treatment for a patient. For this purpose, an elongated connector rod 132 is mounted on a bracket 134 secured to the head end cross member 56 on the thoracic table frame for detachable supportive engagement with a selected one of a plurality of vertically spaced slots 136L, 136M and 136H (FIGS. 4–7), which slots are formed in outwardly facing edges of a pair of L-shaped support adjacent the upper end to opposite side frame members 110 of the head piece frame by pivot pins 140. At the lower end, the support legs are formed with inwardly curving segments 138*a* and these segments are interconnected by a transversely extended elongated cross member or rod 142 (FIG. 8). Support legs 138 have pivot pins 144 mounted on the lower ends for supporting handles 146 which are pivotably mounted thereon.

Figure 4:
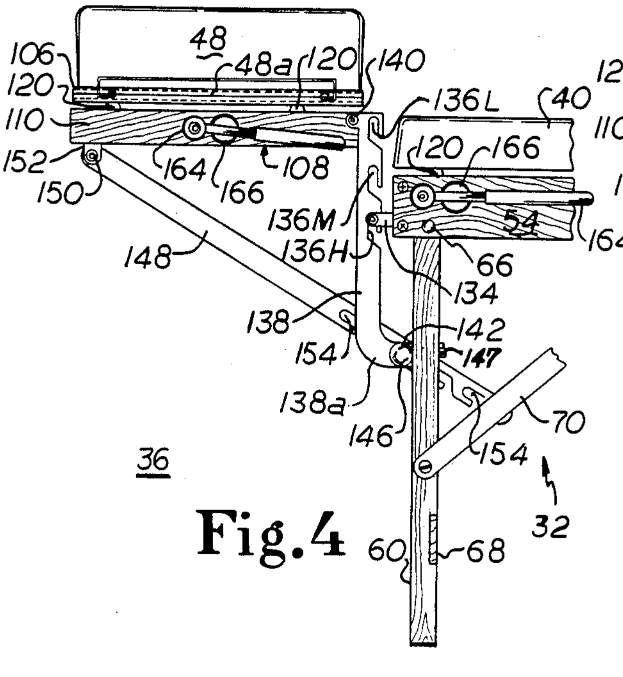
FIG. 4 is a fragmentary side elevational view of a head end portion of the table with a head piece assembly in place thereon at a selected one of a plurality of different head piece levels that are available.
Figure 5:
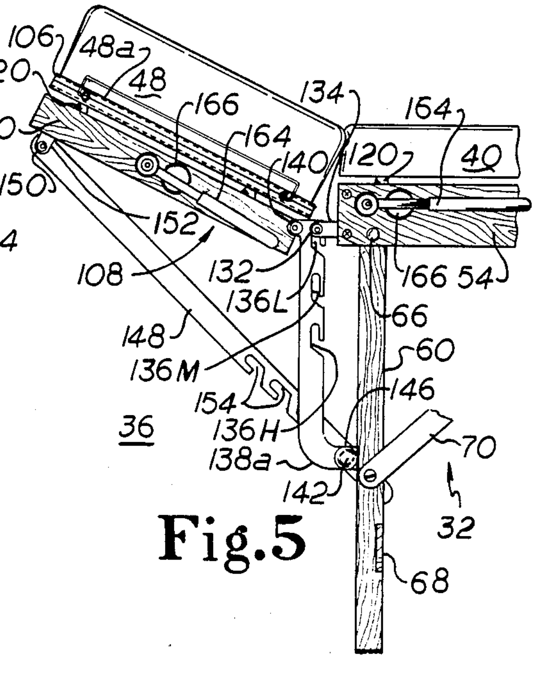
FIG. 5 is a fragmentary side elevational view of a head end portion of the table with the head piece assembly attached and shown in an angularly upwardly sloping position.
Figure 6:
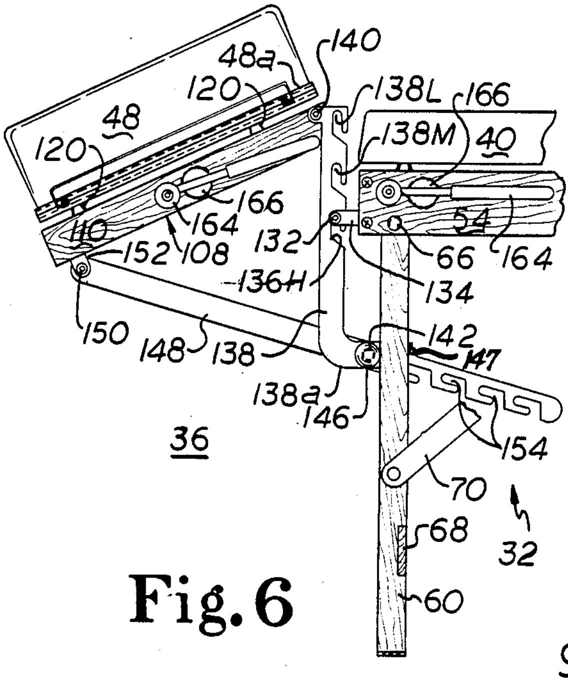
FIG. 6 is a fragmentary side elevational view similar to FIG. 5 illustrating the head piece assembly in an angularly downwardly sloping position for patient treatment.
Figure 7:
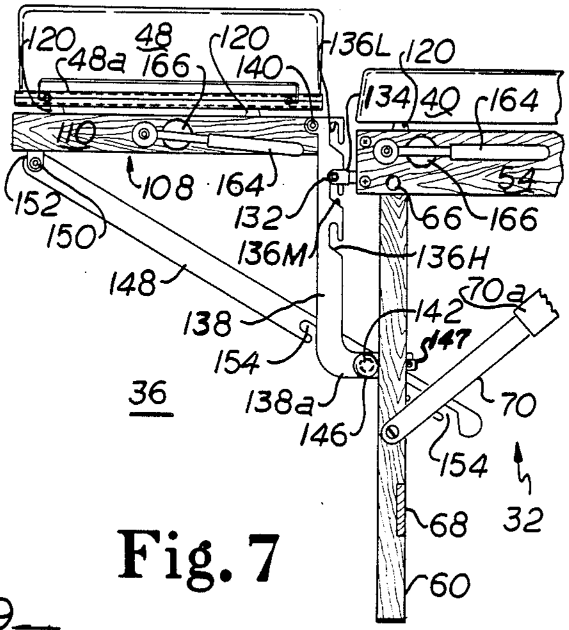
FIG. 7 is a fragmentary side elevational view similar to FIG. 4 but showing the head piece assembly at an intermediate level in a generally horizontal position.
Figure 23:
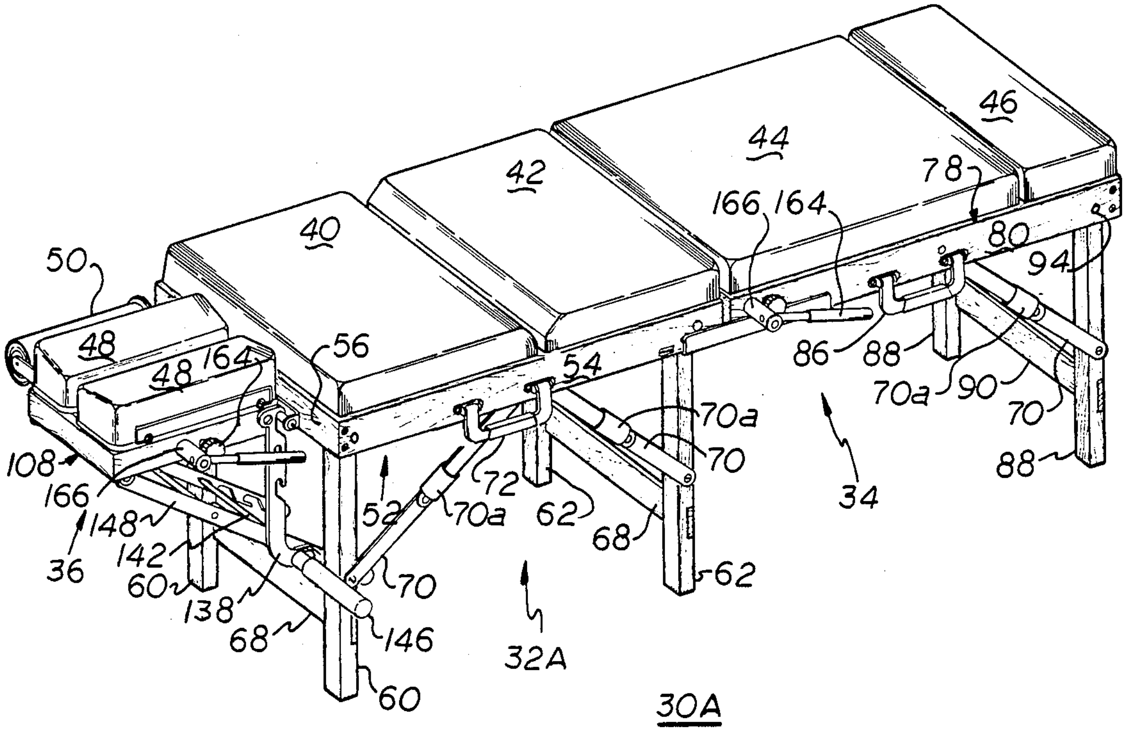
FIG. 23 is a perspective elevational view of another embodiment of a portable treatment table constructed in accordance with the present invention and shown in an assembled condition ready for receiving a patient for treatment.
Figure 24:
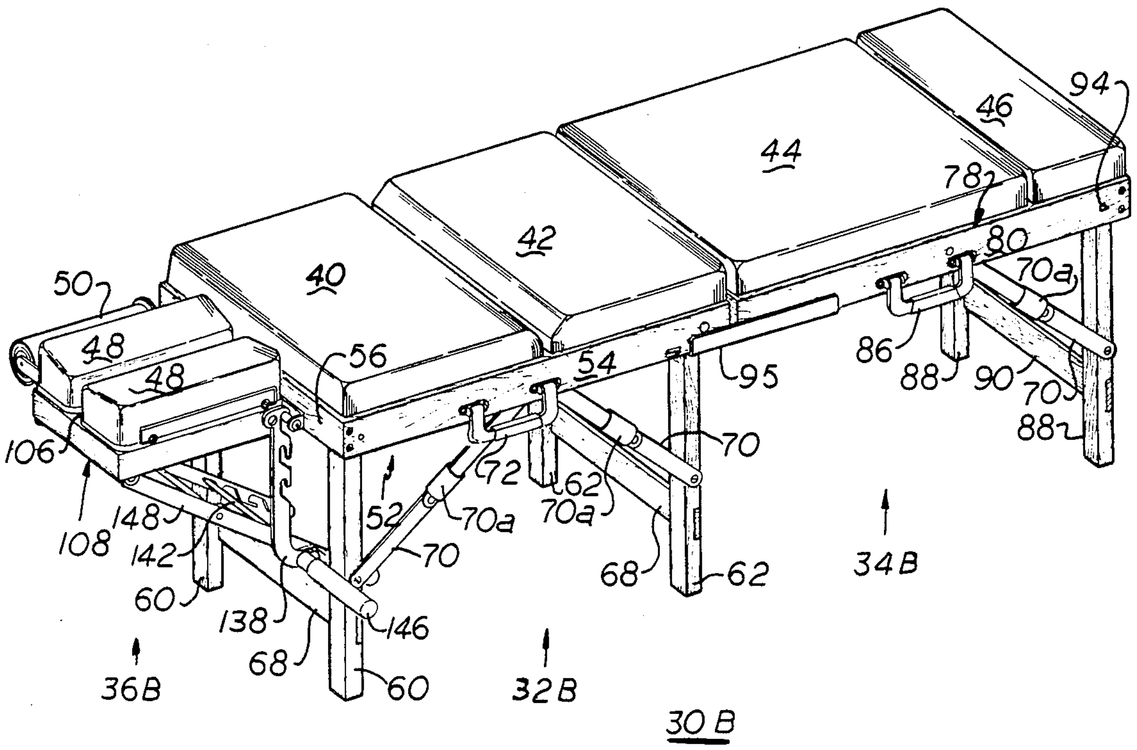
FIG. 24 is yet another embodiment of a portable patient treatment table constructed in accordance with the present invention and shown in an assembled condition ready for receiving a patient for treatment.

The handles are pivoted downwardly into alignment with the rod 142 and are locked in place to extend outwardly of the table section legs 60 as shown in FIGS. 1, 8, 23 and 24. As the handles fold down, short pins 147 which extend through pivot pins 144 supporting the handles also rotate into position behind the legs and restrain the head rest from lifting. The handles 146, when extended outwardly and aligned with the rod 142, provide convenient hand rests for a patient lying face down on the assembled table as shown in FIGS. 2, 23 and 24. In addition, the extended handles serve as stops to engage the forwardly facing edge of the respective front or forward legs 60 of the front table section 32 to support the legs 138 of the head piece with the upper portions in a vertical position. As illustrated in FIGS. 4, 5 and 6, when the slotted out legs 138 are engaged with a selected slot on the support rod 132 of the front table section 32, a preferred elevation or height of the head piece as desired is attained and the weight of the head piece and supporting frame assembly biases the extended handles 146 into engagement with the forwardly facing surfaces of the depending legs 60 to secure the head piece in a stable position with the cross-pins 147 locked against rearwardly facing leg surfaces. The slots 136H, 136M or 136L are chosen to provide a high, medium or low level for the head piece assembly relative to the adjacent dorsal cushion 40 of the front table section 32.

The angular position or slope of the supporting surfaces on the head piece cushions 48 can also be adjusted relative to the horizontal as desired by means of a pair of elongated angle support braces 148 which pivotally interconnected adjacent the upper ends thereof to pins 150 mounted on depending brackets 152 secured to the inside surfaces of the respective side rails 110 of the head piece frame (FIGS. 4–8). The lower end portion of the angle support braces 148 are provided with a series of longitudinally spaced apart, downwardly opening slots 154 adapted for engagement with the cross member rod 142. By selecting a particular set of slots for engagement on the cross member rod 142, the angle or slope of the head piece facial cushions 48 may be adjusted from a generally horizontal position (FIGS. 1, 7, 4, 8, 23 and 24) to an angularly upwardly sloping position (FIG. 5) or downwardly sloping position (FIG. 6) relative to the adjacent dorsal cushion 40 of the front table section 32. It will thus be seen that the head piece assembly 32 when attached to the adjacent front table section 32 may be adjusted both in height or level relative to the table section and may be adjusted to slope up or down thereby providing a wide variety of configurations for treatment of specific ailments of a patient in the cervical area.

Referring momentarily to FIGS. 19 and 20, when the head piece assembly 36 is to be stowed for transport, the support handles 146 are released to pivot inwardly toward a stowing position resting in a longitudinal direction relative to the legs 138 on the head piece support frame 108. Also, the support cushions 48 are removed from the base plate 106 and the elongated support legs 138 and angle support braces 148 are pivoted downwardly into parallelism with the side frame members 110. The base assembly 108 is then stowed on the bottom side of the pelvic cushion 34 which is provided with chocks 156 to align and position the folded-up head piece base between the slides 100. Suitable fasteners such as a "Velcro" strap comprising a pair of flexible, detachably interconnectable elongated fabric strips having areas of compatible, detachable connector hooks and loops thereon or a set of hook and eye fasteners are provided to secure the head piece subassembly in place for transport. The table legs 88 are then folded downwardly to a compact transportable stowed position. The head piece cushions 48 after removal from the base 106 are similarly stowed along with the paper roll assembly 50 on the underside of the cushions 40 and 42 of the front table section 32. The facial cushions are held in a stowed position by "Velcro" type fastener strips 158 (FIGS. 21 and 22) neatly nested between the folded-up legs 60 and 62.

Lift and Drop Assemblies

Referring now more particularly to FIGS. 9–17, each lift and drop assembly 38 includes a base member 160, a J-shaped lift member 162 supported therein, a cocking handle 164 mounted on an outer end portion of the lift member outside the frame and a force adjustment knob 166 adjacent thereto. As illustrated in FIG. 2, the cocking or lift handles 164 are mounted on the same side of the assembled table 30 so that the practitioner can cock the head piece drop, the dorsal cushion drop, the lumbar cushion drop and the pelvic cushion drop mechanisms as desired for selected treatment of a particular patient. Similarly, adjustment knobs 166 are provided for adjusting the amount of downward pressure on the respective cushions that is needed to effect a drop action.

Each base member 160 is provided with an elongated slot adjacent the mounting frame member so that the longer leg of the J-member 162 may rotate freely and the J-shaped member includes an outer end portion projecting outwardly through the adjacent side rail so that the cocking handle or lift handle 164 may be conveniently secured thereto. The short leg of the J-shaped member 162 is adapted to engage a flange portion 168 of a lift plate 170 which, in turn, is engageable with the underside of a respective cushion to be lifted by the cocking of the handle.

The lift plate 170 of each assembly 38 is attached to a downwardly depending lift column 172 mounted in a vertical bore 160*b* in the base 160 and having a stop washer 172*a* at the lower end engageable with the underside of the base 160 to limit upward travel during the lift operation when the handles 164 are rotated in an upward or counterclockwise direction out of the horizontal position as illustrated in FIG. 2. When the handles are cocked as described, the lift plate 170 engages the underside of the respective cushions and causes the cushion to move upwardly into an elevated position ready for a drop.

The lift columns 172 are provided with annular grooves 172*c* and 172*c* and when the lift and drop sections 38 are in a lower or rest position, a spherical detent ball 174 is seated in engagement with the upper groove 172*c* to hold the cushion fixed in place. The amount of pressure exerted by the detent ball in a horizontal direction relative to the axis of the lift column 172 is determined and controlled by a conical recess in a pressure block 176, a coil spring 178, an outer ball 180 and a threaded end portion 182*a* of an adjustment shaft 182 carrying the adjustment knob 166 adjacent an outer end portion. The spherical balls 174 and 180, the pressure block 176, the spring 178 and the shaft 182 are in coaxial alignment within a transversely extending bore 160*a* formed in the base 160 and perpendicular to the vertical bore 160*b* in which the column 172 is mounted for dropping and lifting movement.

A bushing 184 is threaded into the outer end portion of the bore 160*a* and the bushing includes an internal threaded bore for receiving the threaded section 182*a* of the adjustment shaft 182. By tightening the knob 166 in a clockwise direction, the shaft 182 is moved inwardly toward the lift column and increasing pressure is applied to the detent ball 174 seated in one of the grooves 172*c* or 172*c*. When the lift and drop assemblies 38 are cocked by lifting of the handles 164, the J-shaped member 162 causes the lift column 172 to move upwardly until the detent ball 174 is seated in the lower annular groove 172*b*. The amount of pressure exerted by the ball in the groove determines the amount of drop pressure that must be applied on the elevated cushion to move the cushion rapidly downward for a drop action to make the needed chiropractic adjustments on a patient. By tightening or loosening the knob, the desired amount of pressure can be selectively controlled for the drop mechanisms 38.

Referring now to the embodiments of FIGS. 23 and 24, the lift and drop mechanisms 38 are not provided for the dorsal cushion 40 or the lumbar cushion 42 of the front table section 32A and these cushions are instead fixedly secured to the rectangular frame 52. In other aspects, the table 30A is similar in construction and operation to the full featured table illustrated in FIGS. 1 and 2. The table 30B of FIG. 24 is constructed to have no lift and drop features at all and accordingly, the base plate 106 on which the head cushions 48 are detachably mounted, is permanently affixed to the supporting wooden frame 108 and the dorsal cushion 40, lumbar cushion 42 and pelvic cushion 44, respectively, are permanently affixed to the respective frames 52 and 78 of the table sections 32B and 34B.

Cervical Treatment Chair

Figure 16:
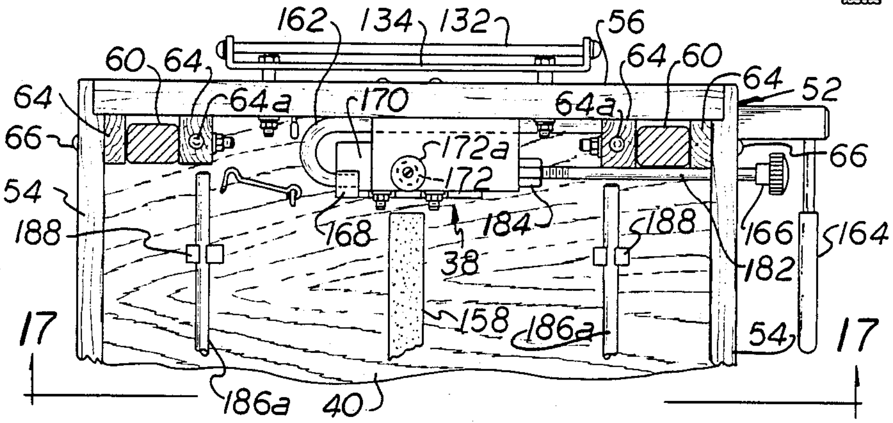
FIG. 16 is a fragmentary bottom view taken substantially along lines 16—16 of FIG. 15.
Figure 17:
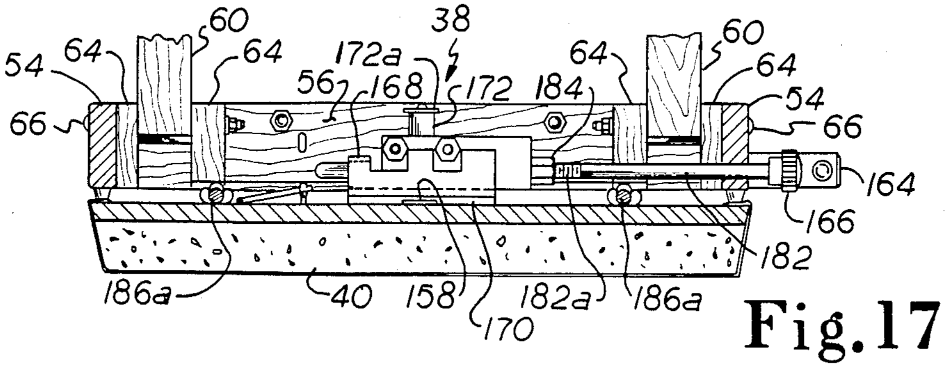
FIG. 17 is a longitudinal cross-sectional view taken substantially along lines 17—17 of FIG. 16.

In accordance with an important feature of the present invention, the front table section 32 of the portable treatment table 30 can also be utilized as a chair for use in palpation or adjustment for a patient in a sitting position on the cushion 42 as illustrated in FIG. 3. When a sitting treatment is to be made, the cushion 40 is pivoted angularly upwardly to the upright position shown and a U-shaped support member 186 having an upper central portion pivotally attached to the underside of the cushion is pivoted so that legs **186*a* are moved outwardly away from the bottom cushion surface and the lower end portion of the legs are seated in sockets 64*a* provided in the corner blocks 64. In normal usage, the U-shaped member is secured in a flat condition to the underside of the dorsal cushion 40 and the legs 186*a* are held in place by clips 188 as shown in FIGS. 16 and 17**.

Many modifications and variations of the present invention are possible in light of the foregoing specification and thus, it is to be understood that within the scope of the appended claims, the invention may be practiced otherwise than as specifically described.

What is claimed and desired to be secured by Letters Patent of the United States is:

1. A portable patient treatment table, comprising:

a plurality of separate, patient body supporting table sections interconnectable for supporting a patient for treatment at a convenient working level above the floor while lying in a generally horizontal position;

each of said table sections including cushion means having an upper surface for supporting a portion of a patient's body and mounted on a frame and a plurality of pairs of supporting legs pivotally interconnected with said frame for movement between a folded-up position inside said frame for transporting said table sections and a downwardly extended position for engagement with the floor to support said cushion means in a treatment position above said floor;

first connector means for detachably interconnecting and securely locking together said frames of said table sections to maintain said cushion means of each of said sections in generally horizontal alignment when all of said legs are extended downwardly;

a head piece including inner and outer end portions for supporting the head of a patient while lying on said cushion means of said interconnected table sections; and second connector means for detachably interconnecting said head piece and one of said table sections with said inner end portion of said head piece positioned adjacent said one table section and said outer end portion spaced outwardly thereof, said second connector means operable to permit said head piece to be completely detached from said one table section for storage inside said folded-up legs of a table section for transportation of said table;

said second connector means including means for interconnecting said head piece at a selected one of several different, generally horizontal levels relative to said upper surface of said cushion means of said one table section and an adjustable support for securing said head piece at a selected one of several different angularly sloping positions relative to said cushion means of said one table section.

2. The portable table of claim 1, wherein:

said head piece includes a frame and at least one head cushion detachably mounted on said frame having an upper surface for supporting a patient's head; and said adjustably support is interconnected between said frame of said head cushion and said one table section for securing said cushion at a selected one of said several angular positions relative to said cushion means of said one table section.

3. The portable table of claim 1, wherein:

said head piece includes at least one head cushion for supporting the head of a patient and a head piece frame for supporting said head cushion; and lift means supportively interconnecting said head cushion and said head frame for holding said head cushion at an elevated position above said head frame and releaseable to permit the rapid drop of said head cushion toward said frame for treatment of a patient in response to a selected level of downward force.

4. The portable table of claim 3, wherein:

said lift means includes control means for elevating said head cushion to said elevated position from a lower position and releaseable detent means for retaining said head cushion in said elevated position until said selected level of downward force is exerted on said head cushion.

5. The portable table of claim 4, wherein:

said releaseable detent means includes manual adjustment means for selecting the level of downward force necessary to drop said head cushion.

6. The portable table of claim 1, wherein:

said interconnecting means includes a pin and slot connector interconnecting said frame of said one table section and said inner end portion of said head piece at said different levels.

7. The portable table of claim 6, wherein said pin and slot connector includes a plurality of elongated connectors on opposite sides of said head piece having longitudinally spaced apart slots for receiving an elongate pin engaging said one table section.

8. The portable table of claim 1, wherein:

said frames of said table sections means are of generally rectangular shape and said plurality of legs of each table section includes at least one pair of legs pivotally connected to opposite sides of said frame to pivot about a common axis and spaced inwardly within said frame.

9. The portable table of claim 8, wherein:
at least one of said table sections includes an additional pair of said legs, said additional pair of legs mounted to pivot about a common axis spaced apart from said common axis of said one pair of legs at an opposite end of said frame.

10. The portable table of claim 8, including:
fastener means on an underside of said cushion means of at least one of said table sections for detachably securing said head piece inside said rectangular shaped frame when said one pair of legs is in a folded up condition.

11. The portable table of claim 10, wherein:
said head piece includes head cushion means detachably mounted on a head piece frame; and
said fastener means includes a fastener on one of said table sections for detachably securing said head cushion means inside said rectangular shaped frame and a fastener on the other of said table sections for detachably securing said head piece frame inside said rectangular shaped frame.

12. The portable table of claim 8, wherein:
said cushion means of at least one of said table sections includes a plurality of separate cushion elements secured to said rectangular frame.

13. The portable table of claim 12, wherein:
one of said cushion elements is supported for sliding movement on said frame toward and away from the other of said cushion elements on said frame to supportively accommodate patients of different height lying on said table when said table sections are interconnected together.

14. The portable table of claim 12, wherein:
at least one of said table sections includes lift means supportively interconnecting said cushion means and said rectangular frame for holding said cushion means at an elevated position above said rectangular frame and releaseable to permit the rapid drop of said cushion means toward said rectangular frame for treatment of the patient in response to a selected level of downward force.

15. The portable table of claim 14, wherein:
said lift means includes control means for elevating said cushion means to said elevated position from a lower position and releaseable detent means for retaining said cushion means in said elevated position until said selected level of downward force is exerted on said cushion means.

16. The portable table of claim 15, wherein:
said releaseable detent means includes manual adjustable means for selecting the level of downward force necessary to drop said cushion means.

17. A portable treatment device for the palpation and adjustment of a patient, in a sitting position, comprising:
a generally rectangular frame;
a plurality of support legs pivotally interconnected adjacent corner portions of said frame for movement between a folded-up position parallel of said frame for transporting said device and a downwardly depending position for supporting a patient seated on said device at a convenient level for treatment above a floor;
a seat cushion covering a first portion of said frame;
a back cushion covering a second portion of said frame adjacent said first portion when in a flat position aligned with said seat cushion;
hinge means pivotally supporting said back cushion for pivotal movement about an axis adjacent an edge of said seat cushion from said flat position toward an upstanding position for supporting the back of a patient sitting on said device; and
support means for interconnecting said frame and said back cushion to support said back cushion in said upstanding position, said support means connected to said back cushion at a position remote from said seat cushion and detachably connected to said frame for securing said back cushion in said upstanding position above said frame for patient treatment.

18. The portable device of claim 17, wherein:
said support means includes a pair of rods spaced apart on opposite sides of said frame and having end portions pivotally secured to said back cushion adjacent an upper end while said back cushion is in said upstanding position and having free lower ends detachable and supported from said rear end member of said frame.

19. The portable device of claim 17, wherein:
said pivot axis is spaced intermediately between opposite front and rear end members of said frame; and wherein
said seat cushion extends forwardly of said axis to said front end member and said back cushion extends rearwardly of said axis to said rear end member when said back cushion is in said flat position.

20. The portable device of claim 19, wherein:
said frame includes at least one frame member extending between said end members for supporting said hinge means.

21. The portable device of claim 17, including:
a separate treatment table section including cushion means for supporting a patient and mounted on a frame, a plurality of support legs pivotally interconnected with said frame for movement between a folded-up condition for transport and a downwardly extending position for engagement with the floor to support said cushion means for patient treatment at a level adjacent said seat cushion of said device; and
first connector means for interconnecting said frames of said device and said table section to support a patient at a convenient working level above the floor while lying in a generally horizontal position.

22. The combination of claim 21, including:
a head piece for supporting the head of a patient while lying on said back and seat cushion of said device and said cushion means of said table section while interconnected together; and
second connector means for detachably interconnecting said head piece and said device.

23. A portable patient treatment table, comprising:
a plurality of separate, patient body supporting table sections interconnectable for supporting a patient for treatment at a convenient working level above the floor while lying in a generally horizontal positional;
each of said table sections including cushion means having an upper surface for supporting a portion of a patient's body and mounted on a frame, and a plurality of pairs of section supporting legs pivotally interconnected with said frame for movement between a folded-up position inside said frame for transporting said table section and a downwardly extended position for engagement with the floor to support said cushion means in a treatment position above said floor;

first connector means for detachably interconnecting and securely locking together said frames of said respective table sections to maintain said cushion means of each of said sections in generally horizontal alignment when all of said legs are extended downwardly;

a head piece including inner and outer end portions for supporting the head of a patient while lying on said cushion means of said interconnected table sections; and second connector means for detachably interconnecting said head piece and one of said table sections with said inner end portion of said head piece positioned adjacent said one table section and said outer end portion spaced outwardly thereof, said second connector means operable to permit said head piece to be completely detached from said one table section for storage inside said folded-up legs of a table section for transportation of said table;

said second connector means including means for interconnecting said head piece at a selected one of several different, generally horizontal levels relative to said upper surface of said cushion means of said one table section and an adjustable support for securing said head piece at a selected one of several different angularly sloping positions relative to said cushion means of said one table section;

said interconnecting means including a pin and slot connector for interconnecting said frame of said one table section and said inner end portion of said head piece at said different levels;

said pin and slot connector including a plurality of elongated connectors on opposite sides of said head piece having longitudinally spaced apart slots for receiving an elongate pin engaging said one table section; and said second connector means including means secured to extend transversely of said plurality of said elongated connectors and engageable with legs of said one table section adjacent said inner end portion of said head piece to prevent pivotal movement of said connectors.

24. The portable table of claim 23, wherein:

said transversely extending means includes hand support means for said patient pivotally movable between an outwardly projecting hand supporting position and a folded-up position for storage.

25. The portable table of claim 23, including:

an adjustable connector for supportively interconnecting said outer end portion of said head piece and said one table section for securing said head piece a selected one of said several different angular sloping positions relative to said cushion means of said one table section.

26. The portable table of claim 25, wherein:

said adjustable support includes a plurality of elongated arms on opposite sides of said head piece having outer ends pivotally secured to said outer end portion of said head piece, said arms including longitudinally spaced apart slots therein for engagement with said elongated pin to secure said head piece in a selected angular slope relative to said one table section.

* * * * *